(12) United States Patent
Mittelstein et al.

(10) Patent No.: US 10,123,905 B2
(45) Date of Patent: Nov. 13, 2018

(54) DEVICES USEABLE FOR TREATMENT OF GLAUCOMA AND OTHER SURGICAL PROCEDURES

(71) Applicant: NeoMedix Corporation, Tustin, CA (US)

(72) Inventors: Michael Mittelstein, Laguna Niguel, CA (US); John T Sorensen, Lake Elsinore, CA (US); Soheila Mirhashemi, Laguna Niguel, CA (US); James B Gerg, Lake Forest, CA (US)

(73) Assignee: NeoMedix, Tustin, CA (US)

( * ) Notice: Subject to any disclaimer, the term of this patent is extended or adjusted under 35 U.S.C. 154(b) by 383 days.

(21) Appl. No.: 14/923,302

(22) Filed: Oct. 26, 2015

(65) Prior Publication Data
US 2016/0106589 A1  Apr. 21, 2016

Related U.S. Application Data

(62) Division of application No. 10/560,266, filed as application No. PCT/US2004/018483 on Jun. 10, 2004.

(Continued)

(51) Int. Cl.
*A61F 9/007* (2006.01)
*A61B 18/14* (2006.01)
(Continued)

(52) U.S. Cl.
CPC ...... *A61F 9/00781* (2013.01); *A61B 18/1402* (2013.01); *A61B 18/1482* (2013.01);
(Continued)

(58) Field of Classification Search
CPC .... A61F 9/007; A61F 9/00781; A61F 9/0079; A61B 18/1402; A61B 18/1482;
(Continued)

(56) References Cited

U.S. PATENT DOCUMENTS 3,776,238 A  12/1973  Peyman et al.
3,882,872 A   5/1975  Douvas et al.
(Continued)

FOREIGN PATENT DOCUMENTS

EP  0073803 A1  3/1983
EP  1455698 A1  9/2004
(Continued)

OTHER PUBLICATIONS

Anderson, "Trabeculotomy compared to goniotomy for glaucoma in children," Ophthalmology, 1983, 90(7), pp. 805-806.
(Continued)

*Primary Examiner* — David Shay
(74) *Attorney, Agent, or Firm* — Robert D. Buyan; Stout, Uxa & Buyan, LLP (57) ABSTRACT

A device and method for cutting or ablating tissue in a human or veterinary patient includes an elongate probe having a distal end, a tissue cutting or ablating apparatus located adjacent within the distal end, and a tissue protector extending from the distal end. The protector generally has a first side and a second side and the tissue cutting or ablating apparatus is located adjacent to the first side thereof. The distal end is structured to be advanceable into tissue or otherwise placed and positioned within the patient's body such that tissue adjacent to the first side of the protector is cut away or ablated by the tissue cutting or ablation apparatus while tissue that is adjacent to the second side of the protector is not substantially damaged by the tissue cutting or ablating apparatus.

7 Claims, 5 Drawing Sheets

Related U.S. Application Data (60) Provisional application No. 60/477,258, filed on Jun. 10, 2003.

(51) Int. Cl.
    *A61B 18/00*     (2006.01)
    *A61B 17/00*     (2006.01)

(52) U.S. Cl.
    CPC ............... *A61B 2017/00526* (2013.01); *A61B 2018/00083* (2013.01); *A61B 2018/00577* (2013.01); *A61B 2018/00601* (2013.01); *A61B 2018/00964* (2013.01); *A61B 2018/1497* (2013.01); *A61B 2218/002* (2013.01); *A61B 2218/007* (2013.01); *A61F 9/007* (2013.01); *A61F 9/0079* (2013.01)

(58) Field of Classification Search
    CPC ........ A61B 2218/002; A61B 2218/007; A61B 2017/00526; A61B 2018/00083; A61B 2018/00577; A61B 2018/00601; A61B 2018/00964; A61B 2018/1497
    USPC .......................................... 606/167, 170, 172
    See application file for complete search history.

(56) References Cited

U.S. PATENT DOCUMENTS

| | | |
|---|---|---|
| 4,011,869 A | 3/1977 | Seiler, Jr. |
| 4,111,207 A | 9/1978 | Seiler, Jr. |
| 4,428,748 A | 1/1984 | Peyman et al. |
| 4,501,274 A | 2/1985 | Skjaerpe |
| 4,559,942 A | 12/1985 | Eisenberg |
| 4,577,629 A | 3/1986 | Martinez |
| 4,649,919 A * | 3/1987 | Thimsen .......... A61B 17/32002 606/170 |
| 4,900,300 A | 2/1990 | Lee |
| 5,042,008 A | 8/1991 | Iwasa et al. |
| 5,163,433 A | 11/1992 | Kagawa et al. |
| 5,222,959 A | 6/1993 | Anis |
| 5,224,950 A | 7/1993 | Prywes |
| 5,431,671 A | 7/1995 | Nallakrishnan |
| 5,478,338 A | 12/1995 | Reynard |
| 5,487,747 A | 1/1996 | Stagmann et al. |
| 5,558,637 A | 9/1996 | Allonen et al. |
| 5,569,283 A | 10/1996 | Green et al. |
| 5,817,115 A | 10/1998 | Nigam |
| 5,865,831 A | 2/1999 | Cozean et al. |
| 6,013,049 A | 1/2000 | Rockley et al. |
| 6,213,997 B1 | 4/2001 | Hood et al. |
| 6,241,721 B1 | 6/2001 | Cozean et al. |
| 6,251,103 B1 | 6/2001 | Berlin |
| 6,264,668 B1 | 7/2001 | Prywes |
| 6,388,043 B1 | 5/2002 | Langer et al. |
| 6,428,501 B1 | 8/2002 | Reynard |
| 6,497,712 B1 | 12/2002 | Feaster |
| 6,720,402 B2 | 4/2004 | Langer et al. |
| 6,759,481 B2 | 7/2004 | Tong |
| 6,764,439 B2 * | 7/2004 | Schaaf ................ A61F 9/00781 600/104 |
| 6,979,328 B2 | 12/2005 | Baerveldt et al. |
| 7,374,566 B1 | 5/2008 | Schossau |
| 7,604,663 B1 | 10/2009 | Reimink et al. |
| 7,632,303 B1 | 12/2009 | Stalker et al. |
| 7,648,591 B2 | 1/2010 | Furst et al. |
| 7,785,321 B2 | 8/2010 | Baerveldt et al. |
| 7,935,131 B2 | 5/2011 | Anthamatten et al. |
| 7,955,387 B2 | 6/2011 | Richter |
| 7,959,641 B2 | 6/2011 | Sorensen et al. |
| 8,038,923 B2 | 10/2011 | Berger et al. |
| 2002/0026205 A1 | 2/2002 | Matsutani et al. |
| 2002/0111608 A1* | 8/2002 | Baerveldt .......... A61F 9/00781 606/6 |
| 2003/0208217 A1 | 11/2003 | Dan |
| 2006/0106370 A1 | 5/2006 | Baerveldt et al. |
| 2006/0149194 A1 | 7/2006 | Conston et al. |
| 2006/0241580 A1 | 10/2006 | Mittelstein et al. |
| 2007/0073275 A1 | 3/2007 | Conston et al. |
| 2007/0276420 A1 | 11/2007 | Sorensen et al. |
| 2009/0248141 A1 | 10/2009 | Shandas et al. |
| 2009/0287233 A1 | 11/2009 | Huculak |
| 2011/0077626 A1 | 3/2011 | Baerveldt et al. |
| 2011/0230877 A1 | 9/2011 | Huculak et al. |
| 2012/0083727 A1 | 4/2012 | Barnett |
| 2015/0045820 A1 | 2/2015 | Kahook |

FOREIGN PATENT DOCUMENTS

| | | |
|---|---|---|
| EP | 1615604 A1 | 1/2006 |
| EP | 2303203 A1 | 4/2011 |
| KR | 20040058309 A | 7/2004 |
| WO | WO2001/078631 A2 | 10/2001 |
| WO | WO2003/045290 A1 | 6/2003 |
| WO | WO2004093761 A1 | 11/2004 |
| WO | WO2004/110501 A2 | 12/2004 |
| WO | WO2009/140185 A1 | 11/2009 |
| WO | WO2011/030081 A1 | 3/2011 |
| WO | WO2013/163034 A1 | 10/2013 |

OTHER PUBLICATIONS

Francis et al., "Ab interno trabeculectomy: development of a novel device (Trabectome®) and surgery for open-angle glaucoma," Journal of Glaucoma, 2006, 15(1), pp. 68-73.

Grant, "Experimental aqueous perfusion in enucleated human eyes," Archives of Ophthalmology, 1963, 69(6), pp. 783-801.

Grant, "Clinical measurements of aqueous outflow," AMA Archives of Ophthalmology, 1951, 46(2), pp. 113-131.

Herschler et al., "Modified goniotomy for inflammatory glaucoma. Histologic evidence for the mechanism of pressure reduction," Archives of Ophthalmology, 1980, 98(4), pp. 684-687.

Jacobi et al., "Technique of goniocurettage: a potential treatment for advanced chronic open angle glaucoma," British Journal of Ophthalmology, 1997,81(4) pp. 302-307.

Jacobi et al., "Goniocurettage for removing trabecular meshwork: clinical results of a new surgical technique in advanced chronic open-angle glaucoma," American Journal of Ophthalmology, 1999, 125(5), pp. 505-510.

Jea et al., "Ab Interno Trabeculectomy Versus Trabeculectomy for Open-Angle Glaucoma," Ophthalmology, 2012, 119(1), pp. 36-42.

Johnson et al., "Human trabecular meshwork organ culture. A new method," Investigative Ophthalmology & Visual Science, 1987,26(6), pp. 945-953.

Minckler et al., "Clinical Results with the Trabectome® for Treatment of Open-Angle Glaucoma," Ophthalmology, 2005, 112(6), pp. 962-967.

Pantcheva et al., "Ab Interno Trabeculectomy," Middle East African Journal of Ophthalmology, 2010, 17(4), pp. 287-289.

Quigley et al., "The number of people with glaucoma worldwide in 2010 and 2020," British Journal of Ophthalmology, 2006, 90(3), pp. 262-267.

Seibold et al., "Preclinical Investigation of Ab Interno Trabeculectomy Using a Novel Dual-Blade Device," American Journal of Ophthalmology, 2013, 155(3), pp. 524-529.e522.

Tan et al., "Postoperative complications after glaucoma surgery for primary angle-closure glaucoma vs primary open-angle glaucoma," Archives of Ophthalmology, 2011,129(8), pp. 987-392.

Skjaerpe, F., "Selective Trabeculectomy. A Report of a New Surgical Method for Open Angle Glaucoma," ACTA Ophthalmologica, vol. 61, pp. 714-727, 1983.

Luntz et al., "Trabeculotomy ab extemo and trabeculectomy in congenital and adult-onset I glaucoma," American Journal of Ophthalmology, 1977, vol. 83, No. 2, pp. 174-179.

Ting et al., "Ab intero trabeculectomy: Outcomes in exfoliation versus primary open-angle I glaucoma," Journal of Cataract & Refractive Surgery, 2012, 38(2), pp. 315-313.

(56) References Cited

OTHER PUBLICATIONS

Dominguez, A., "Ab Interno Trabeculotomy," Bulletins et memoires de la Societe francaise, vol. 86, 1973 (with English Abstract).

* cited by examiner

DEVICES USEABLE FOR TREATMENT OF GLAUCOMA AND OTHER SURGICAL PROCEDURES

RELATED APPLICATIONS

This application is a division of copending U.S. patent application Ser. No. 10/560,266 filed May 11, 2006, which is a 35 U.S.C. § 371 national stage of PCT International Patent Application No. PCT/US2004/018483 Filed Jun. 10, 2004, which claims priority to U.S. Provisional Patent Application No. 60/477,258 filed Jun. 10, 2003, the entire disclosure of each such application being expressly incorporated herein by reference.

BACKGROUND OF THE INVENTION

A. Symptoms and Etiology of Glaucoma

The term "glaucoma" refers generally to a group of diseases which cause progressive damage to the optic nerve and resultant optical field defects, vision loss and, in some cases, blindness. Glaucoma is frequently, but not always, accompanied by abnormally high intraocular pressure. Aqueous humor is continually produced by cells of the ciliary body and such aqueous humor fills the anterior chamber of the eye. Excess aqueous humor normally drains from the anterior chamber of the eye, through a structure known as the trabecular meshwork and then out of the eye through a series of drainage tubules. However, in many glaucoma patients, drainage of the aqueous humor through the trabecular meshwork is impaired, thereby causing the pressure of aqueous humor within the anterior chamber to increase.

In general, there are four types of glaucoma-primary, secondary, congenital and pigmentary. Primary glaucoma, which is the most common form, can be classified as either open angle or closed angle. Secondary glaucoma (e.g., neovascular glaucoma) occurs as a complication of a variety of other conditions, such as injury, inflammation, vascular disease and diabetes. Congenital glaucoma is elevated eye pressure present at birth due to a developmental defect in the eye's drainage mechanism. Pigmentary glaucoma is a rare form of the disease wherein pigment from the iris clogs the trabecular meshwork, preventing the drainage of aqueous humor from the anterior chamber.

Glaucoma is a leading cause of blindness in the United States. The loss of vision in glaucoma patients is typically progressive and may be due, at least in part, to compression of the vasculature of the retina and optic nerve as a result of increased intraocular pressure. It is generally accepted that reducing intraocular pressure, through the use of drugs and/or surgery, can significantly reduce glaucomatous progression in patients who suffer from normal-tension glaucoma and can virtually halt glaucomatous progression in patients who suffer from primary open-angle glaucoma with elevated intraocular pressures. Furthermore, it is generally acknowledged that lowering intraocular pressure in glaucoma patients can prevent or lessen the irreversible glaucoma-associated destruction of optic nerve fibers and the resultant irreversible vision loss.

B. Surgical Treatment of Glaucoma

The surgical treatment of glaucoma is generally aimed at either a) decreasing the amount of aqueous humor produced by the ciliary body or b) improving drainage of aqueous humor from the anterior chamber of the eye.

The procedures aimed at decreasing the production of aqueous humor include cyclocryotherapy, wherein a cryosurgical probe is used to freeze a portion of the ciliary body, thereby destroying cells that produce aqueous humor, and laser cyclophotocoagulation, wherein a laser is used to destroy part of the ciliary body resulting in decreased production of aqueous humor.

The procedures intended to improve drainage of aqueous humor from the anterior chamber include trabeculoplasty, trabeculectomy, goniectomy and shunt implantation.

In trabeculoplasty, the surgeon uses a laser to create small holes through the trabecular meshwork to increase aqueous humor drainage through the normal drainage channels.

In trabeculectomy, the surgeon removes a tiny piece of the wall of the eye, which may include a portion of the trabecular meshwork, thereby creating a new drainage channel which bypasses the trabecular meshwork and the normal drainage channels. Aqueous humor then drains with relative ease through the new drainage channel into a reservoir known as a "bleb" that has been created underneath the conjunctiva. Aqueous humor that drains into the bleb is then absorbed by the body. Trabeculectomy is often used in patients who have been unsuccessfully treated with trabeculoplasty or who suffer from advanced glaucoma where optic nerve damage is progressing and intraocular pressure is significantly elevated.

In goniectomy, a tissue cutting or ablating device is inserted into the anterior chamber of the eye and used to remove a full thickness strip of the tissue from the trabecular meshwork overlying Schlemm's canal. In many cases, a strip of about 2 mm to about 10 mm in length and about 50 µm to about 200 µm in width is removed. This creates a permanent opening in the trabecular meshwork through which aqueous humor may drain. The goniectomy procedure and certain prior art instruments useable to perform such procedure are described in U.S. patent application Ser. No. 10/052,473 published as No. 2002/0111608A1 (Baerveldt), the entirety of which is expressly incorporated herein by reference.

In shunt implantation procedures, a small drainage tube or shunt is implanted in the eye such that aqueous humor may drain from the anterior chamber, through the shunt and into a surgically created sub-conjunctival pocket or "bleb." Aqueous humor that drains into the bleb is then absorbed by the patient's body.

Trabeculoplasty, trabeculectomy and shunt implantation procedures are sometimes unsuccessful due to scarring of closure of the surgically created channels or holes and/or clogging of the drainage tube. Because it involves removal of a full thickness strip from the trabecular meshwork, the goniectomy procedure is less likely to fail due to scarring or natural closure of the surgically created channel. Although the previously described devices can be used to successfully perform goniectomy procedures, there remains a need in the art for the development of new tissue cutting and ablation instruments that may be used to perform the goniectomy procedure as well as other procedures where it is desired to remove a strip of tissue from the body of a human or veterinary patient.

SUMMARY OF THE INVENTION

The present invention provides a device for cutting or ablating tissue in a human or veterinary patient. This device generally comprises, consists essentially of, or consists of: a) an elongate probe having a distal end, b) a tissue cutting or ablating apparatus and c) a protector that extends from the probe. The protector generally has a first side and a second side and the tissue cutting or ablating apparatus is located adjacent to the first side of the protector. The distal end of the probe having protector extending therefrom, is structured to be advanceable into tissue or otherwise placed and positioned within the patient's body such that tissue adjacent to the first side of the protector is cut away or ablated by the tissue cutting or ablation apparatus while tissue that is adjacent to the second side of the protector is not substantially damaged by the tissue cutting or ablating apparatus.

Additionally, the protector may be formed entirely or partially of an insulating material. For example, the protector may be formed of a core made of an electrically and/or thermally conductive material, for example a conductive metallic material, and may include a non-conductive coating or covering, for example a polymer coating that is electrically and thermally insulating. In some embodiments of the invention, the electrically and thermally insulating material, hereinafter sometimes simply referred to as "coating" may comprise a flexible, pliable material in comparison with the more rigid core.

In some embodiments of the invention, the protector is configured not only to provide protection to tissue located adjacent to the second side of the protector, but also may be configured to facilitate positioning and/or advancement of the device within the surgical site. In this particular regard, above-incorporated United States Patent Application No. 2002/0111608A1 (Baerveldt) describes goniectomy devices that have a foot plate sized and configured to be inserted through the trabecular meshwork and into Schlemm's Canal and to, thereafter, advance through Schlemm's Canal as the device is used to remove a portion of the trabecular meshwork. In embodiments of the present invention that are used to remove portions of the trabecular meshwork (i.e., to perform a goniectomy procedure) the protector may be configured, for example shaped and sized, for insertion and advancement through Schlemm's Canal in substantially the same manner as that described in the above-incorporated United States Patent Application No. 2002/0111608A1 (Baerveldt).

It is to be appreciated that in embodiments of the device of the present invention that are designed and/or intended for use in tissue cutting or ablating applications other than goniectomy procedures, the protector may be of any other suitable configuration required to perform the desired protection and/or positioning/guidance functions.

The tissue cutting or ablating apparatus may comprise any suitable type of apparatus that is operative to cut or ablate tissue, for example a strip of tissue. For example, the cutting and ablating apparatus may comprise a electrosurgical or radiofrequency tissue cutting or ablation apparatus (e.g., monopolar or bipolar configured electrodes), apparatus (e.g., a light guide and/or lens) that emits light energy to cause thermal cutting or ablation of tissue (e.g., pulsed or non-pulsed optical incoherent high intensity light, pulsed or non-pulsed laser light, light that is infrared, visible and/or ultraviolet, etc.), mechanical tissue cutting or ablation apparatus (e.g., knife blade(s), scissor(s), rotating cutter(s), etc.), ultrasonic cutting or ablation apparatus (e.g., an ultrasound transmission member that extends through the device to a location adjacent the first side of the protector and undergoes axial or radial ultrasonic vibration), or any other suitable mechanism.

Optionally, the device may further include one or more lumen(s) for providing fluid infusion and/or aspiration to and/or from the surgical site, for example from a remote infusion and/or aspiration source.

In some embodiments of the invention, the device is in the form of an elongate probe that is attachable to a surgical handpiece for facilitating manual manipulation of the probe. In some embodiments of the invention, the entire device is structured and intended for one time use, and in other embodiments of the invention, one or more components of the device are autoclavable and reusable. For example, in some embodiments of the invention, the device comprises a disposable catheter probe having a molded distal end including the protector and/or the cutting or ablating apparatus integrally molded or formed in the distal end of the catheter. In other embodiments of the invention, the device includes a elongate probe, made of one or more segments of stainless steel hypotubing, and including a proximal portion that is configured to be received within a conventional surgical handpiece, which may include various functionable switches, conduit ports, electrical connections and the like for enabling manual operation of the various functions of the device to be described elsewhere herein.

For example, the present device may be configured and structured to be couplable to 1) a console, for example, a control console, or other separate apparatus having for example, but not limited to an electrosurgical signal generator for transmitting energy needed to operate the tissue cutting or ablation apparatus, for example an electrosurgical signal generator suitable for providing electrical energy to the cutting or ablating apparatus utilizing incoherent or laser light energy, such as infrared, visible, and/or ultraviolet wave energy, rotating shaft or other mechanical drive, etc., and/or 2) an aspiration source, for example comprising a pump mechanism for aspirating fluid from the surgical site through the optional aspiration lumen (if present) of the device and/or 3) a source of fluid, for example an irrigation source, for infusing or irrigating the surgical site through the optional fluid infusion lumen (if present) of the device. Examples of commercially available surgical consoles that may be suitable for use with the present invention, for example, surgical consoles of which the present devices may be attached or connected to, include but are not limited to the Infinity/Accurus/Legacy Systems, available from Alcon, Inc., Fort Worth, Tex., the Millinium System, available from the Bausch & Lomb Corporation, Rochester, N.Y., or the Sovereign System, available from Advanced Medical Optics, Santa Ana, Calif.

Further in accordance with the invention, some embodiments of the device may be constructed to cut and remove a strip or pieces of tissue from the patient's body and to permit retrieval of that strip or pieces of tissue to prevent them from causing untoward postsurgical effects within the body or for preservation, biopsy, chemical/biological analysis or other purposes. In embodiments of the device that are equipped with the optional aspiration lumen, the aspiration lumen may be positioned such that a strip or pieces of tissue cut or severed by the tissue cutting or ablation apparatus may be withdrawn from the body through the aspiration lumen.

Still further in accordance with the invention, the width or size of the tissue that is cut or ablated from the patient's body, as well as the degree to which adjacent tissues that remain in the body are damaged by thermal energy or other affects of the cutting or ablation process, may be controlled in some embodiments of the device by controlling the amount of power or energy that is delivered to the tissue cutting or ablation apparatus. In this regard, in embodiments where the tissue cutting or ablation apparatus is a monopolar or bipolar electrosurgical apparatus, there will be a high power density zone closest to the electrode(s) wherein thermal cutting or ablation of tissue will occur. This high power density zone may be surrounded by a medium power density zone wherein the thermal energy is great enough to also cut or ablate tissue under some circumstances. The voltage and/or current supplied to the electrode(s) may be adjusted to control the size and extent of the high power density zone and/or the surrounding medium power density zone, thereby providing for cutting or ablation of a strip of tissue of a desired size while avoiding significant or irreparable damage to tissue that is to be protected (e.g., tissue located on the second side of the protector) or other tissue at the margins of or in close proximity to the strip of tissue that has been cut or ablated.

Still further in accordance with the invention there are provided methods for performing medical or surgical procedures, including percutaneous surgical procedures, using the devices of the present invention. For example, the present invention provides method for performing a goniectomy procedure, wherein the protector of the device, for example the device of the present invention described elsewhere herein, is inserted through the trabecular meshwork into Schlemm's Canal, and the tissue cutting or ablating apparatus is energized and the device is advanced in a manner that results in cutting or ablation of a portion of the trabecular meshwork. In a general tissue cutting procedure, the protector of the device is inserted to a desired position, the tissue cutting or ablation device is energized and the device is advanced, thereby causing a strip to be cut or ablated from tissue that becomes positioned on the first side of the protector while no substantial damage occurs to tissue located on the second side of the protector.

Further in accordance with the invention, some embodiments of the device may be fabricated in part from tubing, such as stainless steel hypotubing (referred to as "tube-fabricated" embodiments. In such tube-fabricated embodiments, the device generally comprises an outer tube and an inner tube, wherein the inner tube extends through the lumen of the outer tube and a distal portion of the inner tube extends out of and beyond the distal end of the outer tube. The protector is formed on the distal end of the inner tube and the tissue cutting or ablation apparatus may be formed on and/or inserted through the inner tube such that it is positioned at a location adjacent to the first side of the protector. Also, the lumens of the inner and/or outer tubes may be used for infusion and/or aspiration of fluid.

Still further in accordance with the invention, there is provided a method for manufacturing the tube-fabricated embodiments of the device. Such method generally comprises A) providing an inner tube and an outer tube and inserting the inner tube through the lumen of the outer tube such that a distal portion of the inner tube extends out of and beyond the distal end of the outer tube, B) forming cuts in the distal portion of the inner tube to form at least one leg thereon, C) bending a leg formed in Step B to create a protector having a first side and a second side and D) positioning the tissue cutting or ablation apparatus adjacent to the first side of the protector. Optionally, in some embodiments, the method may further comprise the step of E) applying an insulating material (e.g., a polymer such as polyimide) to the protector. Such insulating material may be applied to the protector by any suitable method, such as by single layer dip coating, multiple layer dip coating, spray coating, painting, electrostatic powder deposition, vapor deposition, advancement of a fabricated insulating cover over the protector, etc.

Still further in accordance with the invention, in manufacturing some tube-fabricated embodiments wherein the tissue cutting or ablation apparatus comprises an electrosurgical apparatus, an electrode may be formed by additionally cutting and bending a part of the distal portion of the inner tube to form such electrode. In this regard, Step B of the above-summarized manufacturing method may comprise cutting the distal portion of the inner tube to create first and second legs thereon and, thereafter, Step C of the above-summarized manufacturing method may comprise i) bending the first leg to create a protector having a first side and a second side and ii) bending the second leg to create an electrode adjacent to the first side of the protector. Electrical energy may then be transmitted through the inner tube to the electrode formed on its distal portion. In embodiments where the electrosurgical apparatus is monopolar, only one electrode need be formed adjacent to the first side of the protector and an exposed or capacitively coupled grounding electrode may be attached to the patient's body near the site of the surgery or elsewhere on the body. In embodiments where the electrosurgical apparatus is bipolar, it will be necessary to locate a second electrode adjacent to the first side of the protector. Such second electrode may be so positioned by advancing an electrical conduction member that has an electrode surface on its distal end (e.g., an insulated wire having the insulation removed from its distal tip) through the lumen of the inner tube to a position where the electrode surface of the electrical conduction member is located adjacent to the first side of the protector and a desired distance from the other electrode. The electrical conduction member/second electrode may be secured in place by adhesive, mechanical constraint or any other suitable affixation means. In this regard, aperture(s) may be formed in one or both of the leg(s) formed in Step B and the electrically conductive member may extend through such aperture(s) such that the aperture(s) will localize, guide the positioning of, hold, stabilize or affix the location of the electrical conducting member/second electrode.

Further aspects and elements of the invention will be understood by those of skill in the art upon reading the detailed description of specific examples set forth herebelow.

DETAILED DESCRIPTION

Figure 1:
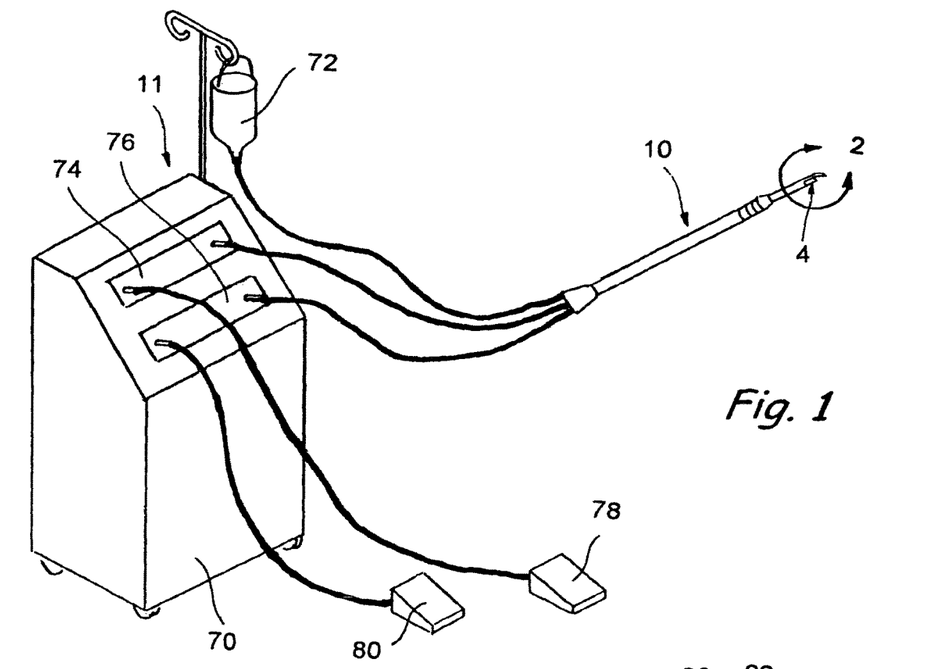
FIG. 1 is a perspective view of a system incorporating an electrosurgical goniectomy device of the present invention.

Turning now to FIG. 1, a device in accordance with the present invention for cutting and/or ablating tissue, for example, tissue of an eye during a goniectomy procedure, is shown generally at 10. The device 10 generally comprises an elongate handpiece or probe having a distal end having a tissue cutting or ablating apparatus 4 disposed generally within the distal end or distal portion of the probe 3. The tissue cutting or ablating apparatus 4 may be a suitable mechanism designed to cut, ablate, cauterize, sever and/or remove tissue from a target region, for example, from a surgical site. The device 10 may be part of a larger surgical system 11, for example, the device 10 may be structured and adapted to be operatively connectable to a separate apparatus, for example a surgical control console 70 for controlling and powering operation of various functions of the device during a surgical procedure. Examples of surgical consoles that may be suitable include but are not limited to the Infinity/Accurus/Legacy Systems, available from Alcon, Inc., Fort Worth, Tex., the Millinium System, available from the Bausch & Lomb Corporation, Rochester, N.Y., or the Sovereign System, available from Advanced Medical Optics, Santa Ana, Calif.

Figure 2:
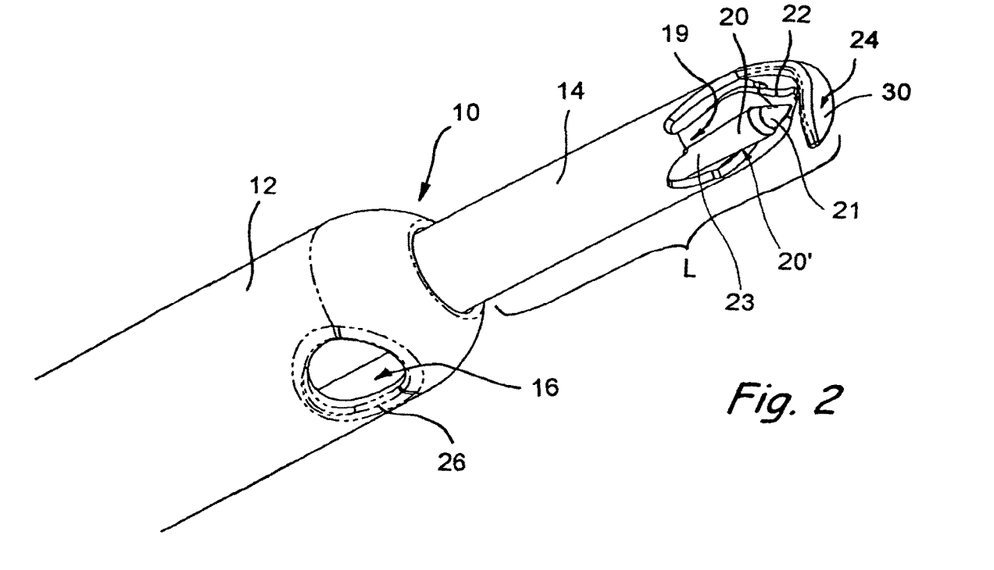
FIG. 2 is an enlarged perspective view of section 2 of FIG. 1.

A distal end of a tube-fabricated embodiment of the device 10 is shown in FIG. 2. This particular device 10 is designed to be especially effective for cutting/ablating and sometimes removing tissue, for example portions of the trabecular meshwork during a goniectomy procedure. It should be appreciated that although the following description will generally refer to this specific embodiment, the scope of the present invention is not intended to be limited thereby. For example, the device 10 may be modified as necessary and/or desirable to be effective for use in surgical procedures other than goniectomy procedures and such modified devices are considered to be within the scope of the present invention.

The tube-fabricated device 10 generally comprises a probe 3 comprising an outer tube 12 and an inner tube 14 disposed therein and having a distal portion extending or projecting therefrom.

As shown in FIG. 2, the inner tube 14 has a smaller outer diameter than an inner diameter of the outer tube 12 such that when inner tube 14 is positioned within the outer tube 12, for example, substantially coaxial therewith, the outer tube 12 inner surface is spaced apart from the inner tube 14 outer surface as shown.

More specifically, the outer tube 12 defines a lumen 16 which may serve as an infusion lumen, hereinafter sometime referred to as an irrigation lumen. For example, the outer tube 12 may include an irrigation or infusion port 26 disposed on the distal portion of the outer tube 12 as shown. During a surgical procedure, irrigation fluid, such as a balanced salt solution (BSS) may be passed through lumen 16 and out of port 26 and into the anterior chamber of an eye as needed to maintain a desired intraocular pressure in the eye.

The inner tube 14 generally contains or defines the cutting or ablating portion of the device 10, as will be described in greater detail elsewhere herein. The inner tube 14 also defines a lumen 19, preferably having a port adjacent the cutting or ablating apparatus, wherein the lumen 19 may serve as an aspiration lumen during the surgical procedure. Accordingly, an aspiration source may be connected to inner tube lumen 19 to allow cut tissue, excess fluid or other material to be suctioned or removed from the surgical site during the procedure.

In embodiments of the device that are designed for cutting or ablating tissue during a goniectomy procedure, the device 10 is preferably sized and configured such that the distal end thereof can be placed within an eye, for example within the anterior chamber of the eye, as far as and including the irrigation port 26. It is noted that irrigation port 26 may alternatively be utilized as an aspiration port in some circumstances, if desirable.

It is further contemplated that in some instances it may be helpful to utilize the aspiration lumen 19 as a temporary or even permanent irrigation lumen such that irrigation fluid is passed from the distal opening of the inner tube 14. For example, as the device 10 is initially being inserted into the anterior chamber prior to the cutting or ablation of tissue, it may be helpful to pass irrigation fluid into the anterior chamber of the eye through the inner tube 14 in order to maintain ocular pressure and facilitate further insertion of the distal end of the relatively wider outer tube 12 of the device 10. Once the distal end of the outer tube 12 is in place in the anterior chamber a sufficiently distance such that port 26 is located within the anterior chamber, irrigation of the eye may be moved to the outer tube irrigation port 26. Initial irrigation by means of the inner lumen 19 may also be helpful in causing gentle widening of the insertion site so as to more easily allow insertion of the relatively wider outer tube through the insertion site.

Preferably, all components of the device 10 are comprised of surgical grade materials. In addition, with the exception of the cutting or ablating surfaces of the device 10, exposed surfaces of the distal end of the device are preferably formed and/or treated such that they include substantially no sharp portions, burrs or contaminants. For example, in the embodiment shown in FIG. 2, the distal most portion of the outer tube 12 is rounded or frustro-conical in shape, so as to prevent or reduce the occurrence of any substantial damage to tissue upon insertion, operation and removal of the device 10 from the eye.

For devices of the invention designed for goniectomy surgical procedures, the outer tube 12 may comprise about 19 gauge to about 20 gauge stainless steel hypotubing, and the inner tube 14 may comprise about 25 gauge stainless steel hypotubing. In addition, preferably for such devices of the invention, the projecting distal portion of the inner tube 14 has a length L of between about 1 mm and about 4 mm, and more preferably about 2.5 mm.

The cutting or ablating portion of the device 10 may comprise any suitable mechanism for cutting or ablating tissue. For example, in the specific embodiment shown in FIG. 2, the cutting or ablating apparatus comprises an electrosurgical tissue cutting/ablating apparatus. More specifically, the device 10 includes a bipolar electrode mechanism comprising a first pole or first electrode 22 and a second pole or second electrode 21. In use, one of the first and second electrodes is provided with electrical energy and to operate as an active electrode and the other of the first and second electrodes operates as a return electrode. When such an electrode is powered it generates a zone of high energy in immediate proximity of the electrode, and a zone of relatively lower energy outside of the zone of high energy. This zone of relatively lower energy is a zone of thermal energy that is effective in cutting or ablating ocular tissue, for instance, particularly tissue of the trabecular meshwork. The return electrode may be electrically couplable to the patient's body.

It is contemplated that alternative embodiments of the invention may include any other suitable mechanism or apparatus that is operative to cut or ablate tissue, for example a strip of tissue, such as a monopolar electrode mechanism, a radiofrequency tissue cutting or ablation apparatus, apparatus (e.g., a light guide and/or lens) that emits light energy to cause thermal cutting or ablation of tissue (e.g., pulsed or non-pulsed optical incoherent high intensity light, pulsed or non-pulsed laser light, light that is infrared, visible and/or ultraviolet, etc.), mechanical tissue cutting or ablation apparatus (e.g., knife blade(s), scissor(s), rotating cutter(s), etc.), ultrasonic cutting or ablation apparatus (e.g., an ultrasound transmission member that extends through the device to a location adjacent the first side of the protector and undergoes axial or radial ultrasonic vibration) or others.

The device 10 further comprises a protector 24 having a first side located adjacent to the cutting or ablating apparatus, and a second side located on a distal-most portion of the device 10. The protector 24 is structured and designed to preventing damage to tissue located near the tissue to be cut. For example, the protector 24 is designed to protect or prevent any substantial damage to surfaces of Schlemm's canal while the device 10 is being utilized to cut portions of the trabecular meshwork during a goniectomy procedure.

More particularly, the device 10 may be structured such that the tissue cutting or ablating apparatus (e.g. the electrode mechanism 20,22) is structured to cause thermal cutting or ablating of tissue and the protector 24 is structured to isolate or protect adjacent tissue located adjacent the second side of the protector 24. For example, the protector 24 may be formed partially or entirely of an insulating material. Alternatively or additionally, the protector 24 may be formed of metal and include a coating 30 made of an insulating material, such as a polymer, for example, a polyimide material.

Turning back now to FIG. 1, the cutting or ablating device 10 may be used as part of a surgical system 11. The system 11 may comprise or consist of a surgical control console 70 including a high frequency electrosurgical generator module 76 and an aspiration pump module 74. A source of irrigation fluid 72 may also be provided which preferably operates as a gravity feed irrigation line. Control of the console 70 during surgical procedures may be accomplished by use of an aspiration footpedal 78 which controls an aspiration pump 74, and use of an electrosurgical footpedal 80 which controls the electrosurgical generator 76. One or both of the footpedals 78 and 80 may be pressure sensitive such that operating power is controllable by the depth or distance at which the footpedal is pressed or moved by the operator. Furthermore, footpedals 78 and 80 may be combined into a single functional unit. The cutting or ablation device 10 may be provided as a pre-sterilized, single-use disposable probe that is attachable to a standard surgical handpiece. After the cutting and ablation device has been attached to the handpiece, further connections to the electrosurgical generator module 76, the aspiration pump module 74 and the source of irrigation fluid 72, may be implemented as shown. Thus, the cutting or ablation device 10 has irrigation, aspiration, and electrosurgical capabilities, as described herein.

A surgical procedure using the device 10 of the present invention may be performed as follows.

Method for Performing Goniectomy

The device 10 and system 11 are useable to perform a variety of procedures wherein it is desired to form an incision or opening of a desired width or to remove, from a mass of tissue, a strip of tissue of a desired width.

Figures 4A, 4B, 4C:
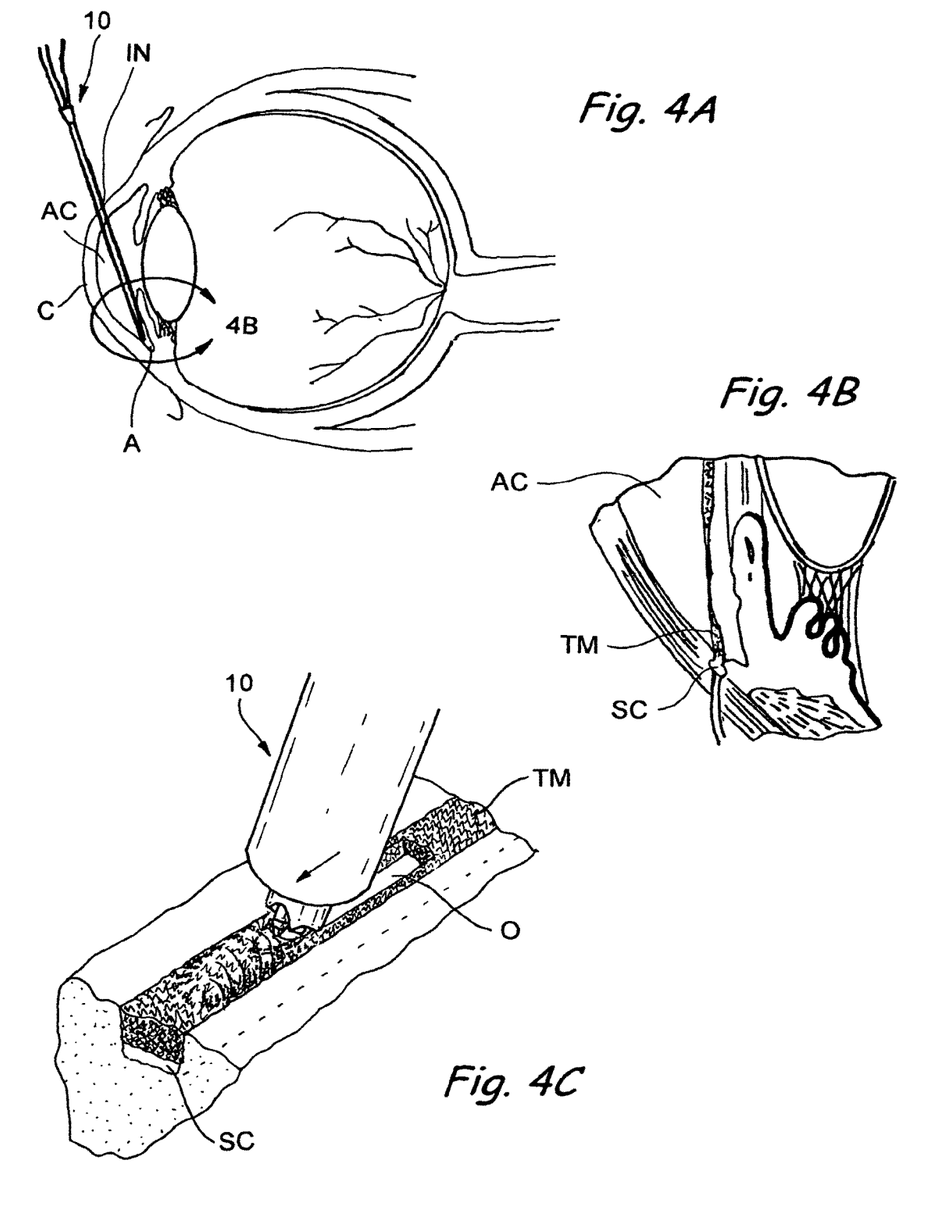
FIG. 4A is a cross section of a human eye having electrosurgical goniectomy device inserted thereinto.
FIG. 4B is an enlarged view of a portion of the human eye showing the angle, Schlemm's Canal and the trabecular meshwork.
FIG. 4C is an enlarged view of a distal portion of the device being used to remove trabecular meshwork tissue from an eye during a goniectomy procedure.

FIGS. 4A-4C, show an example of a goniectomy procedure that may be performed to treat glaucoma, using the device 10 and system 11 of the present invention. This goniectomy procedure is an ab interno surgical procedure wherein a sector of the trabecular meshwork TM is removed from the eye of the patient to facilitate drainage of aqueous humor from the anterior chamber AC of the eye through Shlemm's Canal and the associated collector channels CC, thereby relieving elevated intraocular pressure.

First, a small incision IN is made in the cornea C at about 3 o'clock in the left eye, or at about 9 o'clock in the right eye. A 1.5 mm slit knife may be used to make this incision IN.

The device 10 is attached to the source of irrigation fluid 72 (e.g., balanced salt solution) such that irrigation fluid will flow through lumen 16 of the outer tube 12 and out of outflow aperture 26. The device 10 is then inserted through the incision IN and into the anterior chamber AC (with irrigation flowing). In some cases, during the insertion of the device 10, the source of irrigation fluid 72 may initially connected to the device such that the irrigation fluid will flow through the lumen 19 of the distal portion of inner tube 14. In this manner, irrigation fluid will begin to infuse into the anterior chamber AC as soon as the distal tip of the protruding distal portion of inner tube 14 has entered the anterior chamber AC, rather than being delayed until the larger outer tube 12 and aperture 26 have been advanced through the incision IN and into the anterior chamber. By this alternative approach, irrigation fluid may be caused to flow out of the incision IN as the device 10 is being inserted, thereby spreading or opening the incision. Such spreading or opening of the incision IN may facilitate advancement of the larger diameter outer tube 12 through the incision IN. In cases where this alternative approach is used, the source of infusion fluid 72 will be disconnected from lumen 19 after the device has been inserted into the anterior chamber AC and, thereafter, the infusion fluid source 72 will be reconnected to lumen 16 of outer tube 12 such that infusion fluid will flow out of aperture 26. Negative pressure (e.g., via aspiration pump module 74) may then be applied to lumen 19 of the inner tube 14 so as to aspirate fluid and debris through lumen 19. The vertical height of the infusion fluid source 72 may be adjusted to provide sufficient gravity feed of infusion fluid to make up for the volume of fluid or matter being aspirated from the anterior chamber AC through lumen 19, thereby maintaining the desired pressure of fluid within the anterior chamber AC during the procedure.

A lens device (e.g. Ocular Single Mirror Gonio, Model OSMG, Ocular Instruments, Bellevue, Wash.) may be positioned on the anterior aspect of the eye to enable the physician to clearly visualize the angle A where the segment of trabecular meshwork TM is to be removed. Under such visualization, the device 10 is advanced until the distal tip of the cutter tube or inner tube 14 is positioned adjacent to the trabecular meshwork TM at the location where the strip is to be removed. Thereafter, the protector is advanced through the trabecular meshwork TM and into Schlemm's Canal SC.

The tissue cutting or ablation apparatus, such as bipolar electrodes 21, 22 or 46, 47, is/are then energized and the device 10 is advanced along Schlemm's Canal, thereby causing the cutting or ablation apparatus, such as bipolar electrodes 21 and 22, to cut or ablate a strip of the trabecular meshwork TM to create opening O, as shown in FIG. 4C.

Figure 5A:
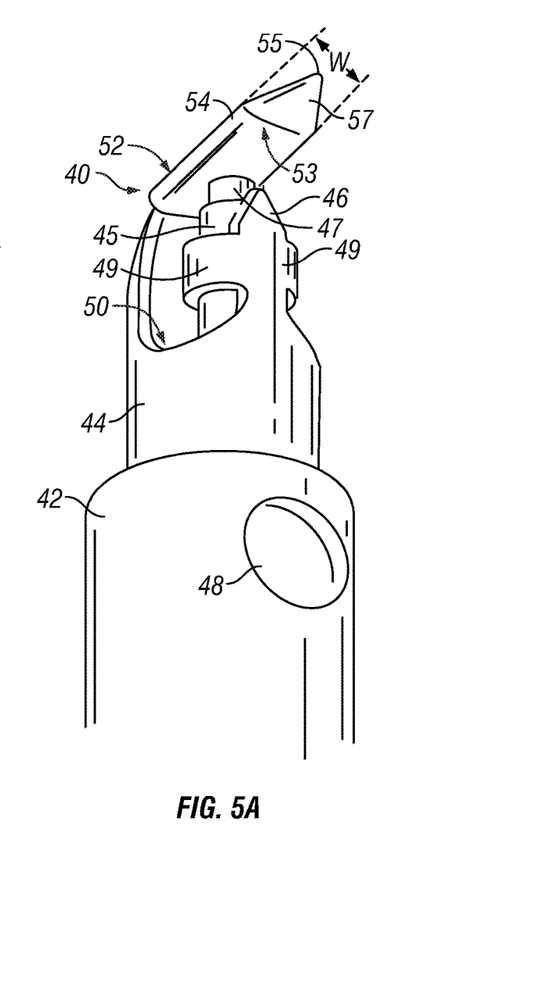
FIG. 5A is a perspective view of a distal portion of another electrosurgical goniectomy device of the present invention.
Figure 5B:
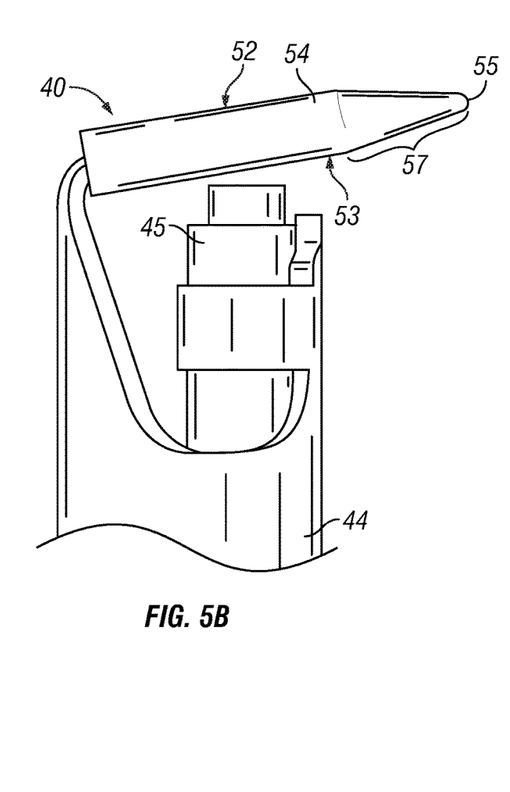
FIG. 5B is a side view of the distal end of the electrosurgical goniectomy device of FIG. 5A.

In the bipolar embodiments of the device 10 shown in FIG. 2 or 5A-5B, discharge of electrosurgical energy via the bipolar electrodes 21, 22 or 46, 47 will remove a full thickness strip of tissue from the trabecular meshwork TM without traumatizing the underlying walls of Schlemm's canal and/or the collector channels, as those structures remain protected from the electrosurgical energy by the advancing protector 24 or 52. The insulated protector 24 or 52 serves two primary purposes: 1) the size and shape of the protector 24 or 52 allows its placement in Schlemm's Canal SC to facilitate guiding the device along Schlemm's Canal SC during the cutting of the strip from the trabecular meshwork TM and 2) the protector 24 or 52 protects and shields the underlying walls of Schlemm's Canal SC and the collector channels from trauma during electrosurgical discharge.

After a strip of tissue of the desired length (e.g., about 2 mm to about 10 mm) has been removed, the tissue cutting or ablation apparatus, such as bipolar electrodes 21, 22 or 46, 47, is/are then de-energized, the aspiration and possibly infusion are stopped and the device 10 is removed from the eye.

Following completion of the surgery, aqueous humor will drain from the anterior chamber AC through the opening O that was created by removal of the strip of tissue from the trabecular meshwork TM.

The present invention further provides a method for manufacturing a device such as tube-fabricated device 10 shown in FIG. 2.

A method in accordance with the present invention for manufacturing the tube-fabricated device 10 generally comprises the steps of providing outer tube 12 and inner tube 14 made of suitable material, for example hypotubing or other material suitable for use in ophthalmic surgery as described elsewhere herein, and inserting the inner tube within the lumen 16 of the outer tube 12 such that a distal portion of inner tube 14 extends or projects a sufficient distance beyond a distal end of the outer tube 12, as shown.

The method further comprises the steps of forming at least one leg on a distal portion of the inner tube 14, for example by beveling the distal end of the inner tube 14 and forming cuts therein and bending the at least one leg to form the protector 24.

FIGS. 3A-3G show the steps involved in manufacturing the device 10 shown in FIG. 2, in accordance with one embodiment of the present invention.

Figure 3A:
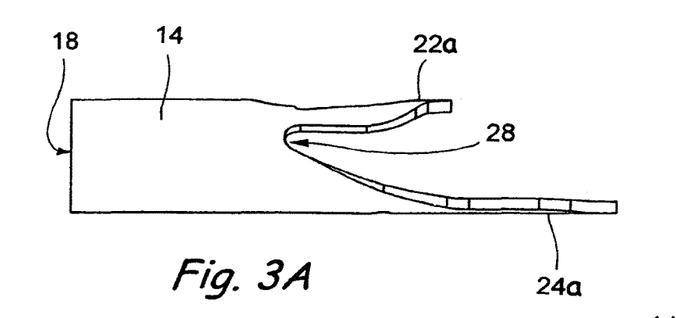
FIGS. 3A-3G are step-by-step showings of an example of a method for manufacturing an electrosurgical goniectomy device of the present invention.

Turning now to FIGS. 3A and 3A', the step of forming at least one leg comprises cutting the distal portion of the inner tube 14, for example, having a beveled distal end of about 45 degrees, to form a first leg 24A and a second leg 22A. The legs 22A and 24A may be formed by cutting substantially U-shaped or V-shaped grooves or notches 28 into the beveled distal portion of the inner tube 14 in order to form relatively longer first leg 24A and a relatively shorter second leg 22A. In this embodiment, the second leg 22A includes a narrow distal tip region and a relatively wider flared region proximal thereto.

Figure 3B:
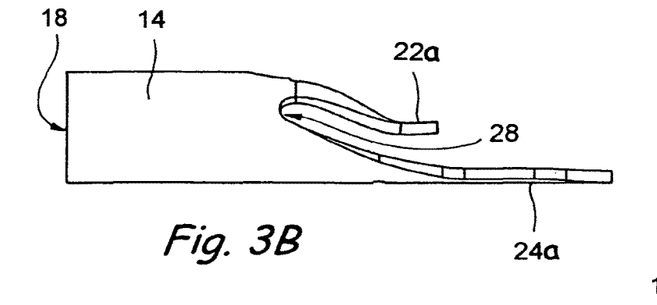

The method may further comprise providing the cutting or ablating apparatus of the device 10 adjacent the first side of the protector 24. More particularly, this step may comprise forming the electrode mechanism from a portion of the inner tube 14, for example, from the second leg 22A. For example, turning now to FIG. 3B, the final position of the second leg 22A is pressed or bent radially inwardly as shown in FIG. 3B such that the distal most tip of the second leg 22A is appropriately positioned to form one pole of the bipolar electrode mechanism. In order to accommodate a second pole of the bipolar electrode mechanism, the method may comprise forming an aperture 19 in the second leg 22A, shown more clearly in FIG. 3B' and passing a wire or other electrically conductive member 20 (hereinafter "electrode member 20") therethrough. The aperture 19 is cut to a size and configuration such that it will accommodate the electrode member 20 such as shown in FIG. 2.

The step of bending the second leg 22A may be accomplished by using tweezers or other suitable tool for gripping and bending the second leg 22A. The distal tip of the second leg 22A (which will form a pole of the electrode) is positioned such that it is substantially aligned with a central axis of the inner tube 14 in the final manufacturing process.

Figure 3C:
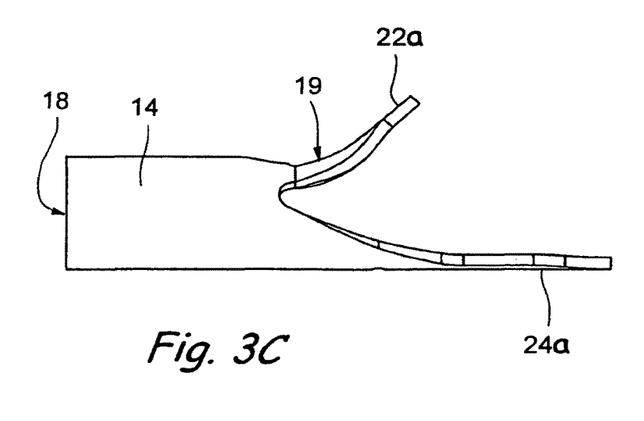

Next, the protector 24 (shown in FIG. 2) may be formed as follows. Second leg 22A is bent slightly radially outwardly, as shown in FIGS. 3C and 3C'. A forming member, for example a pin, wire or other preferably rigid cylindrical member (shown in dashed lines in FIGS. 3C and 3D) is then placed between the first leg 24A and second leg 22A.

Figure 3D:
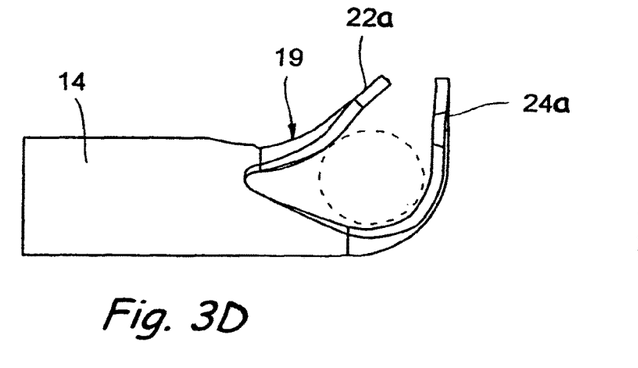

Referring now to FIGS. 3D and 3D', the first leg 24A is pressed, bent or otherwise shaped, for example by using substantially constant radial pressure, around the forming member, to form the curved configuration of first leg 24A shown in FIG. 3D.

Figure 3E:
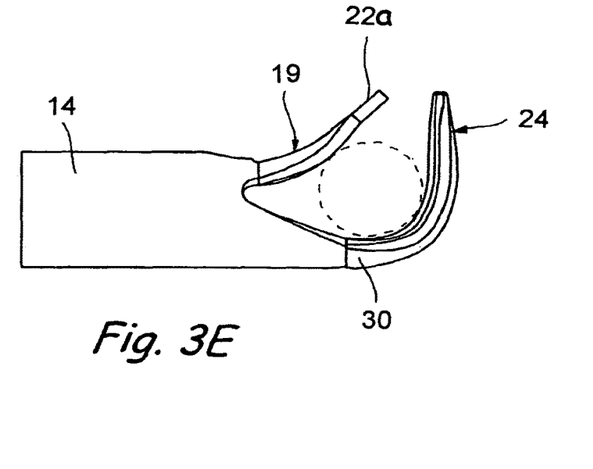

Protector 24, shown in FIGS. 3E and 3E' may be formed by insulating the bent first leg 24A with insulating coating 30. This step may be accomplished using any suitable means, for example, by dip coating, spray coating, or advancement of a fabricated cover over the first leg 24A. The step of insulating or providing insulation may comprise dipping the first leg 22A in a polymer precursor, for example a liquid polyimide, and allowing the liquid polyimide to cure. In some embodiments of the invention, liquid polyimide is applied to both the inside, or first surface, and the outside, or second surface by using a suitable applicator, for example, a tip of a small diameter wire, for example 0.006" diameter wire dipped in a liquid polyimide. In any event, care is taken not to coat the distal tip of second leg 22A.

Figure 3F:
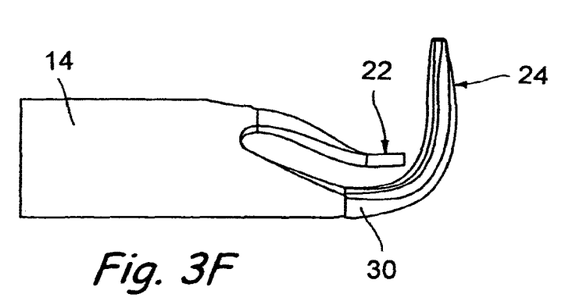

Turning now to FIGS. 3F and 3F', the present invention may comprise the step of forming first electrode 22, (hereinafter sometimes referred to as first pole of bipolar electrode) from distal portion of the inner tube 14. This step may be accomplished by bending second leg 22A radially inwardly, or in some circumstances, allowing second leg 22A to rebound or spring back to its preformed, inwardly bent shape upon removal of the cylindrical forming member (shown in dashed lines in FIGS. 3C and 3D).

As shown, in this particular embodiment, upon being bent inwardly, the distal tip of the second leg 22A is positioned such that it is spaced apart from and adjacent the first side (inside surface) of the protector 24 and is substantially aligned with the central axis of the inner tube 14. The distal most tip of the second leg 22A forms the first pole of the bipolar electrode cutting mechanism.

Figure 3G:
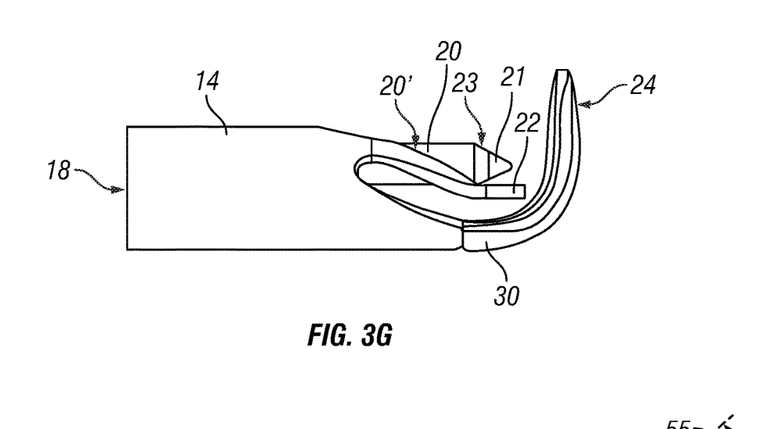

Next, electrode member 20 is inserted or passed through aperture 19 as shown in FIG. 3G such that a distal tip of the electrode member 20 will form the second pole of the bipolar electrode. For example, the first pole and the second pole of the bipolar electrode are preferably spaced apart from each other a distance of about ½₀ mm. The electrodes 21 and 22 are operated to create high temperature region spanning/bridging the electrodes 21 and 22, for example by formation of a high energy plasma. More specifically, the method of the invention may further include the step of providing the electrode member 20 by stripping or removing a distal most portion of an insulated electrically conductive wire in order to expose the conductive portion thereof which will form the second pole or second electrode 21 of the bipolar electrode mechanism. In other words, the electrically conductive member 20 may comprise an insulated wire 20' having insulation 23 stripped or removed from a distal tip thereof as shown in FIG. 2 and FIG. 3G, to expose the electrically conductive tip. Alternatively, the method may comprise providing a non-insulated electrically conductive wire and applying insulation to a proximal portion of the wire while leaving a distal most portion exposed. Such insulation may be applied in a liquid form, for example, the insulation may be applied as liquid polyimide, which is then cured.

Once the second electrode 21 is appropriately placed, electrically conductive member 20 is secured in place, for example by securing the electrically conductive member 20 to the inner tube 14 for example, by adhesive or other suitable means.

The bipolar electrode and the first side of the protector 24 are spaced apart from each other a distance suitable to receive the tissue to be cut by the device 10. It is noted that preferably, in this embodiment of the invention, the distal-most tip of the electrically conductive member 20 is somewhat proximally located with respect to the distal-most tip of the second leg 22A in order to facilitate operation of the device, for example to substantially prevent or reduce the occurrence of tissue becoming unintentionally trapped or wedged within the device. This feature of the invention is shown most clearly in FIG. 3G.

Turning now to FIG. 5A, an alternative distal end 40 of the tube-fabricated embodiment of the invention is shown, including outer tube 42 and inner tube 44 that are similar or substantially identical to outer tube 12 and inner tube 14 described hereinabove with respect to the device 10 shown in FIG. 2.

This alternative distal end may operate in substantially the same fashion as the distal end of device 10 shown in FIG. 2. However, the alternative distal end is formed somewhat differently than the distal end shown in FIG. 2. For example, as seen in FIGS. 5A and 5B, the protector member 54 has first side 53, a second side 52 and a tip 55. The first side 53 of the protector member 54 forms an incline 57 which slopes upwardly from the tip 55. Also, the width W of the protector member 54 tapers to its narrowest point at the tip 55.

The differences may be more readily appreciated by comparing the distal end shown in FIG. 5B with the distal end shown in FIG. 3G. For example, it can be appreciated that second leg 46 (FIG. 5B) which may form a first pole or first electrode of the electrode mechanism, is not bent radially inwardly like second leg 22 (FIG. 3G). In addition electrically conductive member 45 may be positioned or disposed generally along a central axis of the inner tube 44 rather than outwardly therefrom such as electrically conductive member 20. The electrically conductive member 45 includes second pole or second electrode 47 of the electrode mechanism.

As shown, electrically conductive member 45 may be held in place by means of bracket portions 49 formed from portions of second leg 46, as shown. The bracket portions 49 are preferably utilized for facilitating positioning of the electrically conductive member 45 during assembly. Adhesive and/or other means may be provided for securing the electrically conductive member 45 in place.

As shown, outer tube 42 may define an irrigation lumen in fluid communication with irrigation port 48. Inner tube 44 may include aspiration/irrigation lumen 50.

The invention has been described herein with reference to certain examples and embodiments only. No effort has been made to exhaustively describe all possible examples and embodiments of the invention. Indeed, those of skill in the art will appreciate that various additions, deletions, modifications and other changes may be made to the above-described examples and embodiments, without departing from the intended spirit and scope of the invention as recited in the following claims. It is intended that all such additions, deletions, modifications and other changes be included within the scope of the following claims.

What is claimed is:

1. A device that is insertable into the anterior chamber of an eye and useable to form an opening in the trabecular meshwork of that eye, said device comprising:
    an elongate probe having a longitudinal axis and a distal portion that is insertable into the anterior chamber of the eye;
    a protector member on a distal end of the distal portion of the probe, said protector member being oriented in a lateral direction relative to said longitudinal axis and having a first side, a second side and a tip, wherein the first side of the protector member comprises an incline which slopes upwardly from the tip and wherein the protector member has a width which tapers to its narrowest point at the tip; and
    a plurality of knife blades positioned to cut tissue that passes over the first side of the protector member;
    wherein the protector member is configured such that, after an insertion of the distal portion of the elongate probe into an anterior chamber of an eye, the protector member is insertable, tip first, through the trabecular meshwork and into Schlemm's Canal, the distal end of the probe being thereafter moveable in the lateral direction thereby causing the protector member to advance through Schlemm's Canal such that trabecular meshwork tissue passes over the incline and a strip of trabecular meshwork tissue becomes cut by said knife blades.

2. A device according to claim 1 wherein the knife blades are operative to cut a strip of tissue having a width from 50 μm to 200 μm, from the trabecular meshwork.

3. A device according to claim 1 further comprising an irrigation lumen.

4. A device according to claim 1 further comprising an aspiration lumen.

5. A device according to claim 1 further comprising an irrigation lumen and an aspiration lumen.

6. A device according to claim 1 wherein the second side of the protector member is configured so as not to damage tissues adjacent thereto as the protector member is advanced through Schlemm's Canal.

7. A device according to claim 1 wherein said knife blades are located a spaced distance apart to cut a strip of tissue the width of which is substantially equal to the distance between the first and second knife blades.

* * * * *

(12) INTER PARTES REVIEW CERTIFICATE (2943rd)
United States Patent (10) Number: US 10,123,905 K1
Mittelstein et al. (45) Certificate Issued: Dec. 21, 2022

(54) DEVICES USEABLE FOR TREATMENT OF GLAUCOMA AND OTHER SURGICAL PRCEDURES (71) Applicants: Michael Mittelstein; John T. Sorensen; Soheila Mirhashemi; James B. Gerg (72) Inventors: Michael Mittelstein; John T. Sorensen; Soheila Mirhashemi; James B. Gerg (73) Assignee: MICROSURGICAL TECHNOLOGY, INC.

Trial Number:

IPR2021-00065 filed Oct. 16, 2020

Inter Partes Review Certificate for:

Patent No.: 10,123,905
Issued: Nov. 13, 2018
Appl. No.: 14/923,302
Filed: Oct. 26, 2015

The results of IPR2021-00065 are reflected in this inter partes review certificate under 35 U.S.C. 318(b).

INTER PARTES REVIEW CERTIFICATE
U.S. Patent 10,123,905 K1
Trial No. IPR2021-00065
Certificate Issued Dec. 21, 2022

AS A RESULT OF THE INTER PARTES REVIEW PROCEEDING, IT HAS BEEN DETERMINED THAT:

Claims 1-7 are cancelled.

\* \* \* \* \*